United States Patent
Hanna et al.

(10) Patent No.: US 8,980,868 B2
(45) Date of Patent: Mar. 17, 2015

(54) ORAL FORMS OF A PHOSPHONIC ACID DERIVATIVE

(75) Inventors: Mazen Hanna, Lutz, FL (US); Ning Shan, Tampa, FL (US); Miranda Cheney, Tampa, FL (US); David Weyna, Tampa, FL (US)

(73) Assignee: Thar Pharmaceuticals, Inc., Pittsburgh, PA (US)

( * ) Notice: Subject to any disclaimer, the term of this patent is extended or adjusted under 35 U.S.C. 154(b) by 210 days.

(21) Appl. No.: 13/387,490

(22) PCT Filed: Jul. 30, 2010

(86) PCT No.: PCT/US2010/043916
§ 371 (c)(1),
(2), (4) Date: Apr. 13, 2012

(87) PCT Pub. No.: WO2011/014781
PCT Pub. Date: Feb. 3, 2011

(65) Prior Publication Data
US 2012/0190647 A1    Jul. 26, 2012

Related U.S. Application Data

(60) Provisional application No. 61/230,234, filed on Jul. 31, 2009.

(51) Int. Cl.
*A61K 31/675* (2006.01)
*C07F 9/6506* (2006.01)
*A61K 31/195* (2006.01)
*A61K 31/4172* (2006.01)
*A61K 31/401* (2006.01)

(52) U.S. Cl.
CPC ........... *C07F 9/65061* (2013.01); *A61K 31/675* (2013.01)
USPC ............. 514/94; 514/564; 514/400; 514/423; 548/112

(58) Field of Classification Search
None
See application file for complete search history.

(56) References Cited

U.S. PATENT DOCUMENTS

| | | |
|---|---|---|
| 3,959,361 A | 5/1976 | Krueger et al. |
| 3,961,934 A | 6/1976 | Ratts |
| 4,939,130 A | 7/1990 | Jaeggi |
| 2005/0260262 A1 | 11/2005 | Dansereau et al. |
| 2007/0225258 A1 | 9/2007 | Walsh |
| 2008/0254089 A1 | 10/2008 | Glausch et al. |
| 2009/0023683 A1 | 1/2009 | Kocherlakota et al. |
| 2009/0238876 A1 | 9/2009 | Danenberg et al. |
| 2011/0028435 A1 | 2/2011 | Hanna et al. |

FOREIGN PATENT DOCUMENTS

| | | |
|---|---|---|
| WO | 2011014766 A2 | 2/2011 |
| WO | 2011014766 A3 | 2/2011 |
| WO | 2011097269 A1 | 8/2011 |
| WO | 2011097269 A9 | 8/2011 |

OTHER PUBLICATIONS

"Bisphosphonate", Wikipedia, downloaded on Feb. 8, 2014 from "http://en.wikipedia.org/w/index.php?title=Bisphosphonate&oldid=592282031", pp. 1-6 of 6.*
European Search Report for PCT/US2010/043916 dated Jan. 15, 2013.
International Search Report and Written Opinion for PCT International Application No. PCT/US2010/043916, dated Sep. 27, 2010.
U.S. Appl. No. 12/847,568, filed Jul. 30, 2010, Non-Final Rejection, Mailed Jan. 6, 2011.

* cited by examiner

*Primary Examiner* — Savitha Rao
*Assistant Examiner* — Gregg Polansky
(74) *Attorney, Agent, or Firm* — J.A. Lindeman & Co., PLLC

(57) ABSTRACT

Novel solution complexes of zoledronic acid are described which give rise to improved properties of zoledronic acid. The invention includes aqueous solution and molecular complexes of zoledronic acid with and optical isomers of asparagine, histidine, arginine and proline as well as pharmaceutical complexes containing them and methods of treatment using them.

14 Claims, No Drawings

ORAL FORMS OF A PHOSPHONIC ACID DERIVATIVE

CROSS REFERENCE TO RELATED APPLICATION

This application claims priority to PCT International Application No. PCT/US2010/043916, filed Jul. 30, 2010, and U.S. Application No. 61/230,234, filed Jul. 31, 2009, which is incorporated herein by reference.

FIELD OF THE INVENTION

This disclosure pertains to new molecular complexes of zoledronic acid suitable for drug delivery as well as methods for their preparation and pharmaceutical compositions.

BACKGROUND OF THE INVENTION

Zoledronic acid is known as (1-hydroxy-2-imidazol-1-yl-1-phosphono-ethyl)phosphonic acid. Zoledronic acid is depicted by the following chemical structure:

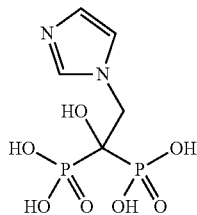 [SMILES: O=P(O)(O)C(O)(Cn1ccnc1)P(=O)(O)O]

Zoledronic acid is a third generation bisphosphonate which far exceeds the previous generations in terms of efficacy and is used predominately for indications of osteoporosis or tumor induced hypercalcemia (TIH). It was originally developed by Novartis and marketed in a monohydrate form under the Zometa® and Reclast® brand names. Zoledronic acid was first approved in 2000 for the treatment of TIH in Canada. It was later approved for use in the US in 2001 for indications of TIH and in 2007 for osteoporosis and Paget's disease. Clinical trials have also been conducted or are on-going exploring the use of zoledronic acid in neoadjuvant or adjuvant cancer therapy, Coleman, et al., British J Cancer 2010; 102(7):1099-1105, Gnant, et al., New England J. Medicine. 2009, 360 (17):679-691 and Davies, et al. J Clinical Oncology, 2010, 28(7s): Abstract 8021. Zoledronic acid is administered as an intravenous (IV) dose of 4 mg over 15 minutes for TIH and 5 mg over 15 minutes for osteoporosis.

Zoledronic acid is sparingly soluble in water and 0.1 N HCl solution but is freely soluble in 0.1 N NaOH. Zoledronic acid is practically insoluble in many organic solvents.

Various efforts have been taken to generate novel oral formulations of zoledronic acid through crystallization and metal salt formation to improve its aqueous solubility, permeability, and subsequent oral bioavailability. A crystalline trihydrate was disclosed in U.S. Patent application 2006/0178439 A1 and world patent application WO2007/032808. Seven hydrated forms, an amorphous form, three monosodium salts, and eleven disodium salts with varying degrees of hydration of zoledronic acid were also disclosed in the world patent application WO2005/005447 A2. Zoledronate metal salts including $Na^+$, $Mg^{2+}$, $Zn^{2+}$ were reported in the monthly issued journal Drugs of the Future (Sorbera et al, 25(3), *Drugs of the Future*, (2000)). Zoledronate, zoledronic, or zoledronic salt represents the ionic form of zoledronic acid. A recently filed patent application (WO2008/064849 A1) from Novartis disclosed additional metal salts including two $Ca^{2+}$ salts, two $Zn^{2+}$ salts, one $Mg^{2+}$ salt, as well as a mono and trihydrate, an amorphous form, and an anhydrous form.

The low oral bioavailability of zoledronic acid, which is <1% of the oral dose, can be attributed to poor permeability in the gastrointestinal (GI) tract. It was also noted that insoluble metal complexes were formed in the upper intestines, most commonly with calcium. Zoledronic acid has also been shown to cause severe GI irritation both in the stomach and in the intestines. In some cases the irritation was so severe that medical treatment was required. Recent activity concerning the development of oral formulations has led to the use of medium chain fatty acids to enhance the drug's low permeability as disclosed in the US 2007/0134319 A1 and US 2007/0196464 patent applications. Modified amino acid carriers, but not pure proteinogenic amino acids, have also been employed to improve the absorption of the drug as shown in the WO 2007/093226 A1 application.

In general, sparingly water soluble, provides substantial challenges for drug development of parenteral formulations due to the amount of solvent needed to dissolve the drug which could render it more suitable for infusion. Typically, the greater the volume needed to be administered parenterally to a patient, the longer the infusion time, the higher the likelihood of a vehicle-related adverse effect, the more expensive the product, and the less likelihood that the formulation will be found acceptable by the patient. By improving the aqueous solubility of the drug the volume of solvent needed for reconstitution can therefore be dramatically reduced rendering it suitable for injection rather than infusion.

Due to the fact that zoledronic acid is only available as a parenteral dosage form (infusion over at least 15 minutes) there is a clear need to develop novel forms of zoledronic acid that can be included in an oral dosage form particularly as the use of orally administered drugs are becoming more wide spread in many therapeutic areas including the treatment of cancer. The upward trend in the use of oral drugs will continue especially in light of the goal to decrease the overall cost of healthcare. Thus, there is an opportunity to create oral dosage forms of IV drugs only where oral dosage forms do not yet exist due to their poor aqueous solubility and/or poor permeability providing a clear clinical benefit for patients. In addition, opportunity is also provided to improve the solubility of sparingly water soluble drugs by creating molecular complexes of such drugs with standard (proteinogenic) amino acids that can subsequently be incorporated in dosage forms for a variety of drug delivery systems.

The development of oral forms of zoledronic acid to enhance the aqueous solubility or permeability has thus far been problematic. However, by using the novel approach of generating molecular complexes of zoledronic acid with standard amino acids there is an opportunity provided to improve the solubility and/or permeability resulting in a new dosage form suitable administration to humans.

SUMMARY OF THE INVENTION

The present disclosure is directed towards generating new molecular complexes of zoledronic acid that have the therapeutic efficacy of zoledronic acid but also improved aqueous solubility, rate of dissolution, and improved bioavailability. One aspect of the present disclosure relates to novel molecular complexes of zoledronic acid. In addition, the disclosure further includes methods for the preparation of such complexes. The disclosure further includes compositions of molecular complexes of zoledronic acid suitable for incorporation in a pharmaceutical dosage form. Specific molecular complexes pertaining to the disclosure include, but are not limited to, complexes of zoledronic acid with nicotinamide, adenine, glycine, and optical isomers of asparagine, histidine, argenine, and proline; D or L-asparagine, DL-asparagine, D or L-histidine, DL-histidine, D or L-arginine, DL-arginine, D or L-proline and DL-proline. Variants of the disclosed zoledronic acid forms in the text, including those described by the examples, will be readily apparent to the person of ordinary skill in the art having the present disclosure, and such variants are considered to be a part of the current invention.

The foregoing and other features and advantages of the disclosed technology will become more apparent from the following detailed description. Such description is meant to be illustrative, and not limiting, of the invention.

DETAILED DESCRIPTION OF THE PREFERRED EMBODIMENTS

In general, the active pharmaceutical ingredient (API) in pharmaceutical compositions can be prepared in a variety of different forms. Such compounds can be prepared so as to have a variety of different chemical forms including chemical derivatives, solvates, hydrates, cocrystal salts, etc. The API can also have different physical forms. For example, they may be amorphous or they may have different crystalline polymorphs or may exist in different solvated or hydrated states. The discovery of new forms of an API may provide the opportunity to improve the pharmacokinetic performance of a pharmaceutical product. Additionally, pharmaceutical cocrystallization can expand the array of resources available for designing, for example, a pharmaceutical dosage form of a drug with a targeted release profile or other desired characteristics.

The physical form of the API has been shown to have a substantial impact upon its physicochemical properties. For example, crystalline polymorphs typically have different aqueous solubility from one another, such that a more thermodynamically stable polymorph is less soluble than a less thermodynamically stable polymorph. In addition to water solubility, pharmaceutical polymorphs can also differ in properties such as rate of dissolution, shelf-life, bioavailability, morphology, vapor pressure, density, color, and compressibility. Accordingly, it is desirable to enhance the properties of an API by forming molecular complexes with respect to aqueous solubility, rate of dissolution, bioavailability, Cmax, Tmax, physicochemical stability, down-stream processibility (e.g. flowability compressibility, degree of brittleness, particle size manipulation), crystallization of amorphous compounds, decrease in polymorphic form diversity, toxicity, taste, production costs, and manufacturing methods.

During the development of drugs for oral delivery, it is frequently advantageous to have novel forms of such drug materials that possess improved properties, including increased aqueous solubility and stability. It is also desirable in general to increase the dissolution rate of such solid forms, and potentially increase their bioavailability. This also applies to the development of novel forms of zoledronic acid which, when administered orally to a subject could achieve greater or similar bioavailabilities and pharmacokinetic (PK) profiles when compared to an IV or other formulations on a dose-for-dose basis.

Novel solution complexes of zoledronic acid in the present invention could give rise to improved properties of zoledronic acid. For example, a new form of zoledronic acid is particularly advantageous if it can improve the aqueous solubility and subsequent bioavailability of orally delivered zoledronic acid. A number of novel zoledronic acid forms have been synthesized, characterized, and disclosed herein. The aqueous solubility of zoledronic acid is low but has been dramatically increased in this invention up to greater than 350 mg/ml through creating new molecular complexes with cocrystal formers including such as nicotinamide, amino acids, and in particular with adenine, glycine, L-asparagine, DL-asparagine, L-histidine, DL-histidine, L-arginine, DL-arginine, L-proline, DL-proline. The techniques and approaches set forth in the present disclosure can further be used by the person of ordinary skill in the art to prepare obvious variants thereof, said variants are considered to be part of the inventive disclosure.

Accordingly, a first aspect of the present invention includes aqueous solution complexes of zoledronic acid with amino acids, including but not limited to adenine, glycine, and optical isomers of asparagine, histidine, argenine and proline. Preferred amino acids include but are not limited to nicotinamide, adenine, glycine, L-asparagine, DL-asparagine, L-histidine, DL-histidine, L-arginine, DL-arginine, L-proline, and DL-proline suitable for coformulation in an oral dosage form, as a solution, suspension, or a solution in capsules ether incorporated in a gel structure or polymer matrix. These pharmaceutical formulations contain a therapeutically effective amount of at least one solution complex of zoledronic acid according to the invention and at least one pharmaceutically acceptable carrier, (also known in the art as a pharmaceutically acceptable excipient). The novel molecular complexes of zoledronic acid are therapeutically useful for the treatment and/or prevention of disease states associated with osteoporosis, tumor induced hypercalcemia (TIH), or Paget's disease as discussed above. Accordingly, the invention also relates to methods of treatment using novel molecular complexes of zoledronic acid of the invention or a pharmaceutical formulation containing them. The pharmaceutical formulations generally contain about 1% to about 99% by weight of at least one novel molecular complex of zoledronic acid of the invention and 99% to 1% by weight of a suitable pharmaceutical excipient.

Another aspect of the invention includes improving the aqueous solubility of zoledronic acid to greater than 350 mg/ml, through creating new molecular complexes with L- and DL-histidine.

Another aspect of the invention includes improving the aqueous solubility of zoledronic acid to greater than 235 mg/ml, through creating new molecular complexes with L- and DL-arginine.

Another aspect of the invention includes improving the aqueous solubility of zoledronic acid to greater than 50 mg/ml, through creating new molecular complexes with L- and DL-asparagine.

Another aspect of the invention where the solution complexes of zoledronic acid with amino acids. Solution complexes of zoledronic acid and optical isomers of asparagine, histidine, arginine and proline; L-asparagine, DL-asparagine, L-histidine, DL-histidine, L-arginine, DL-arginine, L-proline, and DL-proline were physically stable and did not form any suspension or create precipitates when examined by the naked eye after being left standing at room temperature on the bench in screw cap vials for one year.

Another aspect of the invention provides complexes of zoledronic acid and optical isomers of asparagine, histidine, arginine and proline; L-asparagine, DL-asparagine, L-lysine, DL-lysine, nicotinamide, adenine, glycine, L-histidine, DL-histidine, L-arginine, DL-arginine, L-proline, and DL-proline suitable for a pharmaceutical formulation than can be delivered parenterally to the human body.

Another aspect of the invention provides a method for increasing the aqueous solubility of a bisphosphonic acid or bisphosphonates by dissolving a bisphosphonic acid or bisphosphonate in an aqueous solvent in the presence of an amino acid such as those discussed above. The bisphosphonic acid may be, for example, zoledronic acid, clodronic acid, tiludronic acid, pamidronic acid, alendronic acid, residronic acid ibandronic acid or other bisphosphonic acids known in the art.

EXAMPLES

The following examples illustrate the invention without intending to limit the scope of the invention.

Zoledronic acid as a starting material used in all experiments in this disclosure was supplied by Farmkemi Limited (Wuhan Pharma Chemical Co.), China with purity of ca. 90% and was purified further via recrystallization from hot water. All other pure chemicals (Analytical Grade) were supplied by Sigma-Aldrich and used without further purification.

Example 1

Preparation of a Solution of Zoledronic Acid:L-Histidine 7.8 mg of zoledronic acid and 9.5 mg of L-histidine were mixture and dissolved in 0.05 ml water. The solution containing the complex was stored in a screw cap vial.

Example 2

Preparation of a Solution of Zoledronic:DL-Histidine Complex 17.8 mg of zoledronic acid and 9.5 mg of DL-histidine were mixed and dissolved in 0.05 ml water. The solution containing the complex was stored in a screw cap vial for subsequent analysis and use.

Example 3

Preparation of a Solution of Zoledronic:L-Arginine Complex 35.6 mg of zoledronic acid and 21.4 mg of L-arginine were mixed and dissolved in 0.15 ml water. The solution containing the complex was stored in a screw cap vial for subsequent analysis and use.

Example 4

Preparation of a Solution of Zoledronic:DL-Arginine Complex 35.6 mg of zoledronic acid and 21.4 mg of DL-arginine were mixed and dissolved in 0.15 ml water. The solution containing the complex was stored in a screw cap vial for subsequent analysis and use.

Example 5

Preparation of a Solution of Zoledronic:L-Asparagine Complex 50 mg of zoledronic acid and 23 mg of L-asparagine were dissolved in 1 ml water. The solution containing the complex was stored in a screw cap vial for subsequent analysis and use.

Example 6

Preparation of a Solution of Zoledronic:DL-Asparagine Complex 50 mg of zoledronic acid and 26 mg of DL-asparagine monohydrate were dissolved in 1 ml water. The solution containing the complex was stored in a screw cap vial for subsequent analysis and use.

Example 7

Preparation of a Solution of Zoledronic:L-Proline Complex

Approximately 11 mg of zoledronic acid and approximately 9 mg of L-proline were mixed and dissolved in 1 ml water. The solution containing the complex was stored in a screw cap vial for subsequent analysis and use.

Example 8

Preparation of a Solution of Zoledronic:DL-Proline Complex

Approximately 11 mg of zoledronic acid and approximately 9 mg of DL-proline were mixed and dissolved in 1 ml water. The solution containing the complex was stored in a screw cap vial for subsequent analysis and use.

The claimed invention is:
1. A solution complex of zoledronic acid comprising zoledronic acid and a coformer selected from the group consisting of asparagine, histidine, arginine and proline to improve the aqueous solubility of the zoledronic acid.
2. A solution complex of claim 1, wherein the amino acid is selected from the group consisting of L-asparagine, DL-asparagine, L-histidine, DL-histidine, L-arginine, DL-arginine, L-proline, and DL-proline.
3. A solution complex of claim 2, wherein the complex is:
   a solution complex of zoledronic acid and L-histidine having an aqueous solubility of zoledronic acid to greater than 350 mg/ml,
   a solution complex of zoledronic acid and DL-histidine having an aqueous solubility of zoledronic acid to greater than 350 mg/ml,
   a solution complex of zoledronic acid and L-arginine having an aqueous solubility of zoledronic acid to greater than 235 mg/ml,
   a solution complex of zoledronic acid and DL-arginine having an aqueous solubility of zoledronic acid to greater than 235 mg/ml,
   a solution complex of zoledronic acid and L-asparagine having an aqueous solubility of zoledronic acid to greater than 50 mg/ml, or
   a solution complex of zoledronic acid and DL-asparagine having an aqueous solubility of zoledronic acid to greater than 50 mg/ml.

4. A pharmaceutical composition comprising a complex of claim 1 and a pharmaceutically acceptable carrier.

5. A pharmaceutical composition of claim 4, wherein the composition is a parenteral composition.

6. A pharmaceutical composition of claim 4, wherein the composition is an oral dosage form.

7. A method for the treatment of disease states associated with osteoporosis, tumor induced hypercalcemia (TIH), or Paget's disease comprising the step of administering to a patient in need thereof a therapeutically effective amount of a pharmaceutical composition of claim 4.

8. A method for the treatment of disease states associated with osteoporosis, tumor induced hypercalcemia (TIH), or Paget's disease, adjuvant or neoadjuvant cancer therapies comprising the step of administering to a patient in need thereof a therapeutically effective amount of a complex according to claim 1.

9. A method for increasing the aqueous solubility of zoledronic acid comprising the step of:

dissolving zoledronic acid in an aqueous solvent in the presence of an amino acid selected from the group consisting of asparagine, histidine, arginine and proline.

10. A method of claim 9, wherein the amino acid is selected from the group consisting of L-asparagine, DL-asparagine, L-histidine, DL-histidine, L-arginine, DL-arginine, L-proline, and DL-proline and wherein the amino acid forms a solution complex with the zoledronic acid.

11. A method of claim 9, wherein the aqueous solvent is water.

12. A pharmaceutical composition comprising a complex of claim 3 and a pharmaceutically acceptable carrier.

13. A method for the treatment of disease states associated with osteoporosis, tumor induced hypercalcemia (TIH), or Paget's disease, adjuvant or neoadjuvant cancer therapies comprising the step of administering to a patient in need thereof a therapeutically effective amount of a complex according to claim 3.

14. A method of claim 9, wherein the aqueous solvent is water.

* * * * *